(12) United States Patent
Dayton

(10) Patent No.: US 9,889,219 B2
(45) Date of Patent: Feb. 13, 2018

(54) DECONTAMINATION APPARATUS AND METHOD

(71) Applicant: Daylight Medical, Inc., Middleburg Heights, OH (US)

(72) Inventor: Roderick Dayton, Strongsville, OH (US)

(73) Assignee: DIVERSEY, INC., Charlotte, NC (US)

( * ) Notice: Subject to any disclaimer, the term of this patent is extended or adjusted under 35 U.S.C. 154(b) by 0 days.

(21) Appl. No.: 15/398,166

(22) Filed: Jan. 4, 2017

(65) Prior Publication Data
US 2017/0112954 A1    Apr. 27, 2017

Related U.S. Application Data

(63) Continuation-in-part of application No. PCT/US2015/060047, filed on Nov. 10, 2015.

(60) Provisional application No. 62/421,505, filed on Nov. 14, 2016, provisional application No. 62/077,512, filed on Nov. 10, 2014.

(51) Int. Cl.
*A61L 2/26* (2006.01)
*A61L 2/10* (2006.01)

(52) U.S. Cl.
CPC .......... *A61L 2/26* (2013.01); *A61L 2/10* (2013.01); *A61L 2202/14* (2013.01); *A61L 2202/16* (2013.01); *A61L 2202/25* (2013.01)

(58) Field of Classification Search
CPC ..... A61L 2/08; A61L 2/10; A61L 2/24; A61L 2/26; A61L 2202/14; A61L 2202/16; A61L 2202/25
See application file for complete search history.

(56) References Cited

U.S. PATENT DOCUMENTS

| | | | |
|---|---|---|---|
| 8,516,651 B2 | 8/2013 | Jones et al. | |
| 2005/0065675 A1* | 3/2005 | Georgi | A61G 5/043 701/23 |
| 2005/0273967 A1* | 12/2005 | Taylor | A47L 5/28 15/319 |
| 2012/0260944 A1* | 10/2012 | Martins, Jr. | A47L 5/14 134/18 |
| 2012/0282135 A1* | 11/2012 | Trapani | A61L 2/10 422/3 |
| 2012/0305787 A1 | 12/2012 | Henson | |
| 2013/0270459 A1* | 10/2013 | Fontani | A61L 2/10 250/492.1 |
| 2014/0330452 A1* | 11/2014 | Stewart | B25J 11/0085 701/2 |
| 2016/0136314 A1* | 5/2016 | Kreitenberg | A61L 2/10 422/24 |
| 2016/0271803 A1* | 9/2016 | Stewart | B25J 11/0085 |

OTHER PUBLICATIONS

International Search Report and Written Opinion dated Mar. 24, 2016 for PCT/US2015/060047.

* cited by examiner

*Primary Examiner* — David E Smith
(74) *Attorney, Agent, or Firm* — Cooper Legal Group, LLC

(57) ABSTRACT

Provided is a decontamination apparatus that includes a motorized base with a transport system that is operable to autonomously move the decontamination apparatus. A plurality of UVC bulbs, each of which emits UVC light, are supported at a vertical elevation above the motorized base. A controller controls operation of the transport system to move the decontamination apparatus along a desired route while the UVC bulbs are energized during a decontamination process.

18 Claims, 10 Drawing Sheets

DECONTAMINATION APPARATUS AND METHOD

BACKGROUND OF THE INVENTION

1. Field of the Invention

This disclosure relates generally to a system, apparatus, and method for decontaminating a plurality of surfaces, and optionally gathering information on ultraviolet energy at a variety of physical locations in a given environment and providing that information to a collection point for graphic display, analysis, and recording.

2. Description of Related Art

High touch environmental surfaces in healthcare facilities are recognized as significant sources of pathogens. To avoid exposing patients in such environments to infectious organisms, medical personnel working therein are required to take precautionary measures to disinfect high touch surfaces. One such measure is to expose entire rooms, in which the high touch surfaces reside, to disinfection technologies that employ high doses of ultraviolet light in the C spectrum, UVC. These high doses may be from continuous or pulsed sources, but one challenge with these technologies is to ensure that substantially all surfaces are suitably exposed to the UVC to achieve the desired level of pathogen reduction.

BRIEF SUMMARY OF THE INVENTION

Accordingly, there is a need in the art for a method and apparatus for exposing surfaces in a room to a sufficient level of UVC light to achieve a predetermined level of pathogen reduction on the surfaces. Such a system and method can optionally utilize a plurality of relatively low-power UVC light sources that are automatically repositioned to expose to UVC light various surfaces that are originally shielded from the UVC light while the decontamination apparatus is positioned at a starting location within the room.

The method and apparatus can optionally utilize sensors that, in real time, detect and provide meaningful data on the intensity experienced at given points and to record these data for purposes of qualifying and improving the efficacy of disinfection efforts. Such a method and apparatus can capture a plurality of data points of UVC intensity, optionally simultaneously and/or concurrently, present the data in real time, record the data for future analysis, and improve the accuracy and quality of delivered disinfection technology for use in medical applications.

According to one aspect, the subject application involves a decontamination apparatus that includes a motorized base with a transport system that is operable to move the decontamination apparatus. A plurality of UVC bulbs that each emit UVC light are supported by the base. A controller stores a learned route to be traveled by the decontamination apparatus from a starting point to a destination during a decontamination process and controls operation of the transport system to move the decontamination apparatus along the learned route.

According to another aspect, the subject application involves a method of capturing UVC data points for use in a medical application. The method includes detecting UVC levels at various locations with at least one sensor sensitive to UVC, each sensor having a communication capability to provide UVC intensity information to a central device.

According to another aspect, each UVC sensor is designed such that it may be battery powered.

According to another aspect, each UVC sensor is designed such that it may be temporarily affixed to a location where intensity measurement is desirable.

According to another aspect, each UVC sensor is designed such that it may be permanently affixed to a location that allows it to be powered from a wall outlet.

According to another aspect, each UVC sensor is designed such that it may only detect a specific band of energy.

According to another aspect, the subject application involves sensors that have a wide angle of sensitivity (e.g., at least X°) to input such that materially significant impinging UVC is measured even off the direct axis.

According to another aspect, the central data collection point is designed such that it is able to monitor multiple sensor input simultaneously.

According to another aspect, the central data collection point is designed such that it can collect data form the sensors through wireless communication.

According to another aspect, the central data collection point is designed such that it can report the collected data in various units of measure.

According to another aspect, the central data collection point is designed such that it can report data collected in real time.

According to another aspect, the central data collection point is designed such that it can be customized to include data uniquely identified to a specific sensor, room number, operator, etc.

According to another aspect, the subject application involves a method of capturing these UVC data points when used in a manufacturing application. The method includes multiple sensors sensitive to UVC with each sensor having a communication capability to provide UVC intensity information to a central device.

According to another aspect, the subject application involves a decontamination apparatus that includes a motorized base comprising a transport system that is operable to move the decontamination apparatus over a floor. A plurality of UVC bulbs, each configured to emit UVC light, are supported at an elevation vertically above the motorized base. A sensor detects a marking on the floor defining a desired route to be traveled by the motorized base during a decontamination process, and a controller controls operation of the transport system to move the motorized base supporting the plurality of UVC bulbs over the floor along the desired route defined by the marking.

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

BRIEF DESCRIPTION OF SEVERAL VIEWS OF THE DRAWING

The invention may take physical form in certain parts and arrangement of parts, embodiments of which will be described in detail in this specification and illustrated in the accompanying drawings which form a part hereof and wherein.

DETAILED DESCRIPTION OF THE INVENTION

Figure 1:
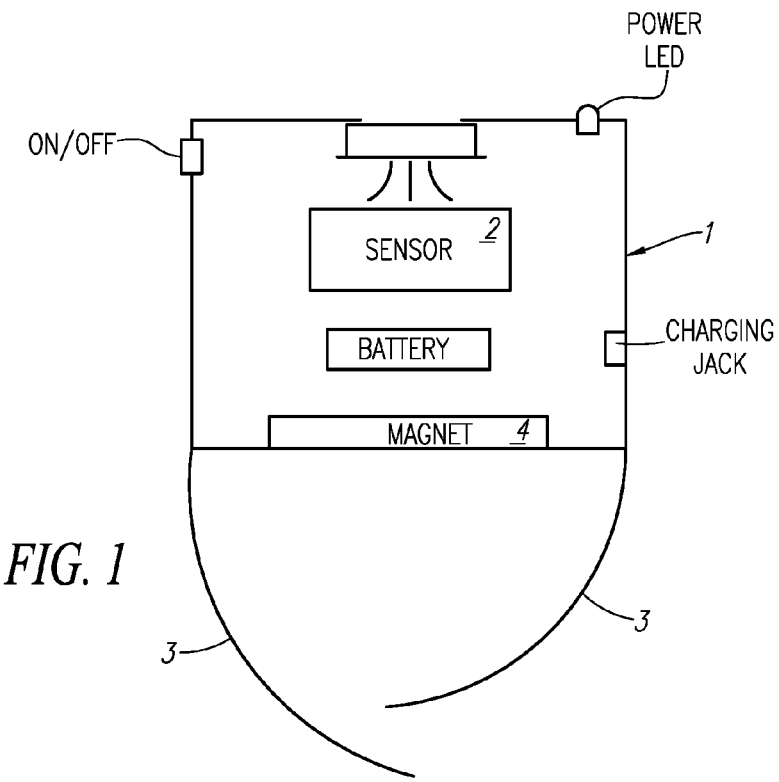
FIG. 1 shows a perspective view of an illustrative embodiment of a UVC sensor.

Certain terminology is used herein for convenience only and is not to be taken as a limitation on the present invention. Relative language used herein is best understood with reference to the drawings, in which like numerals are used to identify like or similar items. Further, in the drawings, certain features may be shown in somewhat schematic form.

It is also to be noted that the phrase "at least one of", if used herein, followed by a plurality of members herein means one of the members, or a combination of more than one of the members. For example, the phrase "at least one of a first widget and a second widget" means in the present application: the first widget, the second widget, or the first widget and the second widget. Likewise, "at least one of a first widget, a second widget and a third widget" means in the present application: the first widget, the second widget, the third widget, the first widget and the second widget, the first widget and the third widget, the second widget and the third widget, or the first widget and the second widget and the third widget.

In order to disinfect surfaces in healthcare facilities (e.g., beds in patient rooms, tray tables, seats, etc.), high doses of UVC are provided from a source during an irradiation process. Currently, irradiation protocols must be tested to ensure that each part of the area is sufficiently disinfected. However, various layouts of rooms and shapes of furniture can make it difficult to expose each surface to be decontaminated to an adequate level of UVC to achieve the desired level of pathogen reduction. This often requires manually positioning a centrally-located, high-power UVC source at a desired location in the room, activating the UVC source to perform irradiation at one location, once irradiation is complete and the source deactivated, manually moving the source, and once again activating the source to irradiate again. This process is often repeated multiple times to ensure sufficient exposure of all surfaces to the UVC light, but is labor intensive and time consuming, rendering such protocols impractical. Thus, the present disclosure is directed to a system, apparatus, and method for sequentially exposing various different surfaces to UVC light, and optionally gathering information on ultraviolet energy at a variety of physical locations in a given environment and providing that information to a collection point for graphic display, analysis, and recording.

One aspect of the present disclosure pertains to UVC sensors that can optionally be positioned at various locations in a room with surfaces to be decontaminated to sense the level of exposure to UVC light. One example of a UVC sensor 1 is shown in FIG. 1. The UVC sensor 1 includes an optical sensor 2 that senses UVC light 3 and transmits a signal indicative of the intensity, power output, or other property of UVC light indicative of the sterilization effectiveness of that UVC light to which the sensor 2 is exposed. The optical sensor 2 can be positioned at any suitable location where it is expected to be exposed to the UVC light transmitted by a UVC source, or where it is necessary to determine the exposure of UVC light. In some embodiments, the UVC sensor can be sensitive to only a specific, narrow band of UVC frequencies. Furthermore, it is desirable that the UVC sensor is capable of sensing UVC light at large incidence angles such that the sensor does not need to be directly in line of site of the UVC source.

In some embodiments, hook and loop straps 3, a magnetic mount 4, the like, or some combination thereof may be provided in order to mount the UVC sensors 1 in a variety of locations and to a variety of objects. In various embodiments, the UVC sensors 1 may be temporarily mounted to test the efficacy of an irradiation protocol for a room layout. However, in other embodiments, it may be desirable to permanently mount the UVC sensors 1. Depending on whether a UVC sensor is temporarily or permanently mounted, it may be desirable to have a removable, rechargeable, or wired power source such as a lithium ion battery. Further in this vein, FIG. 1 indicates an on/off power switch and power LED indicator such that the UVC sensors can be turned on only during an irradiation process.

Figure 2:
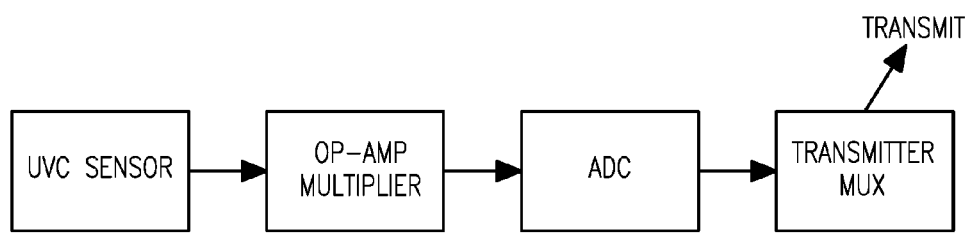
FIG. 2 shows a block diagram of the sensor operation.
Figure 4:
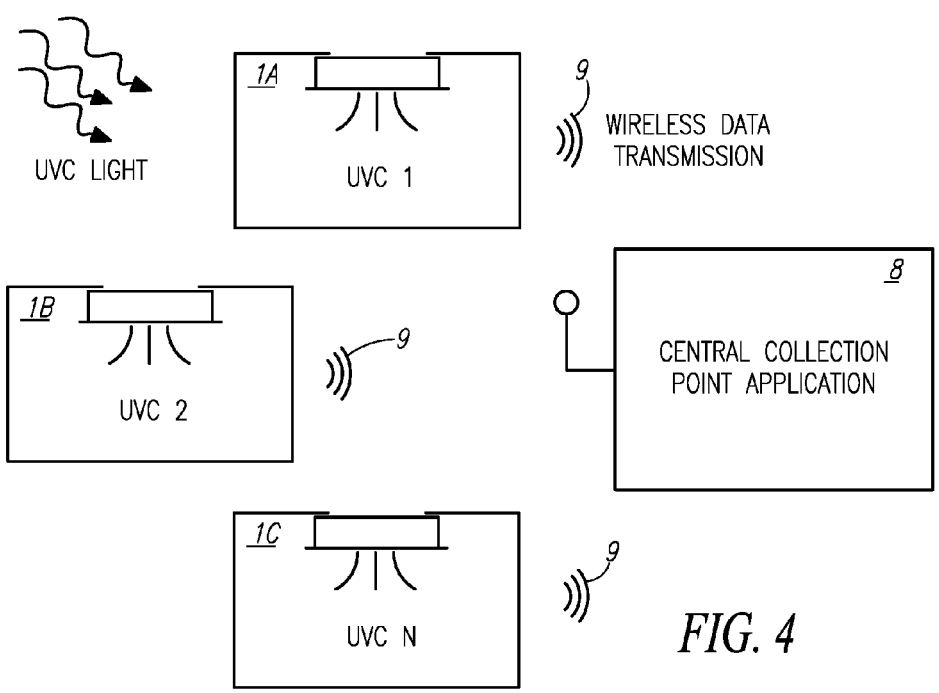
FIG. 4 shows a flow diagram graphically illustrating the connectivity and action between the sensors and the central collection point.

FIG. 2 illustrates a flow chart of the UVC sensor 1 operation. According to the flow chart, a signal from the optical sensor 2 is passed to an opamp multiplier 5. Next, the signal is converted to a digital signal by an analog to digital converter 6, before the signal is multiplexed and transmitted by a transmitter 7. As further illustrated in FIG. 4, multiple UVC sensors 1A, 1B, 1C may work together to generate and report data related to UVC irradiation. In some embodiments, each UVC sensor 1A, 1B, 1C may transmit, via a wireless communication channel 9 (e.g., IEEE 802.11, Bluetooth, etc.) data directly to a tablet 8 or similar personal computing device, which can generate a graphical representation of the collected data for convenient viewing by a clinician. However, in other embodiments, the UVC sensors may transmit data to a central collection point. In such an embodiment, the sensors may only transmit data to the central collection point in an industrial, scientific, and medical (ISM) band. In this way, transmissions from the UVC sensors can be on the order of megahertz, thereby saving power consumption at the UVC sensor. In contrast, WiFi and Bluetooth technologies, which are often most compatible with personal computing devices, transmit in gigahertz bandwidths requiring additional power. The central collection point may then collect all of the data from the UVC sensors and forward it to a tablet or other computing device using WiFi or nearfield Bluetooth technologies.

Figure 3:
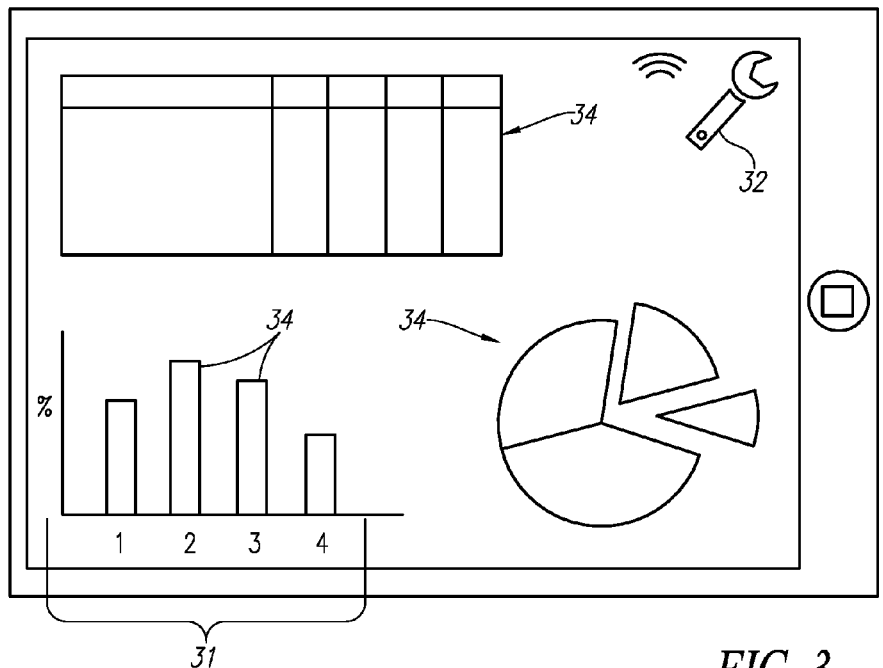
FIG. 3 shows a graphic representation of the central collection point display and representative data fields.

FIG. 3 illustrates an example of how the UVC sensor data may be displayed on a tablet or similar device. In this example, one section of the screen illustrates a bar graph 31 for illustrating the intensity of light measured at each UVC sensor. Each bar 34 on the bar graph 31 can represent a UVC sensor. The bars may change color (e.g., green to yellow to red) indicating whether the detected UVC is at an adequate level. In some embodiments, the bars 34 are customizable. For example, a first bar may represent a UVC sensor placed on a bed requiring one level of UVC irradiation. Another bar may represent a sensor placed on a wall across the room requiring a second level of UVC irradiation. Accordingly, the color coding of each bar may be specific to the required customized irradiation levels required. A table section 35 may indicate a current irradiation level for each sensor and/or an irradiation intensity accumulation over time (i.e., shown in Joules or Watts). Also shown is a pie chart section 35 for showing similar data. Of course, the above represents but a few examples of what data may be illustrated and how that data be illustrated, but does not represent a limiting embodiment. Other data collected by the UVC sensor may be displayed in various formats as known to those skilled in the art. The application for displaying the UVC sensor data may also comprise a settings screen (accessible by button 32, but not otherwise shown). As discussed above, in many embodiments the application on the computing device interfaces with the UVC sensors and/or the central collection point using WiFi or Bluetooth technologies, but any communication technology is envisioned within the scope of the present disclosure.

The embodiments described above utilize an array of sensors to detect the extent to which different regions of a room are exposed to UVC light emitted by a stationary decontamination apparatus. In addition to displaying data, it is also envisioned that the UVC sensors could be used to automatically control a motorized decontamination apparatus that travels to a plurality of different locations throughout the room. That is, for example, if one UVC sensor detects a less than adequate level of UVC to achieve a predetermined level of pathogen reduction specified by the user, it could transmit a signal that directs the decontamination apparatus to autonomously move in such a way that the location of the reporting UVC sensor receives additional irradiation. For example, the decontamination apparatus can travel along a straight-line path towards the requesting UVC sensor or along a programmed path as described herein to approach the requesting sensor. Other embodiments are also envisioned that use the UVC sensors as a safety mechanism during periods of irradiation. That is, for example, if a UVC sensor detects UVC at a time when no irradiation is supposed to be underway, it may be used to alert all individuals in the area of the potentially-hazardous condition.

Figure 5:
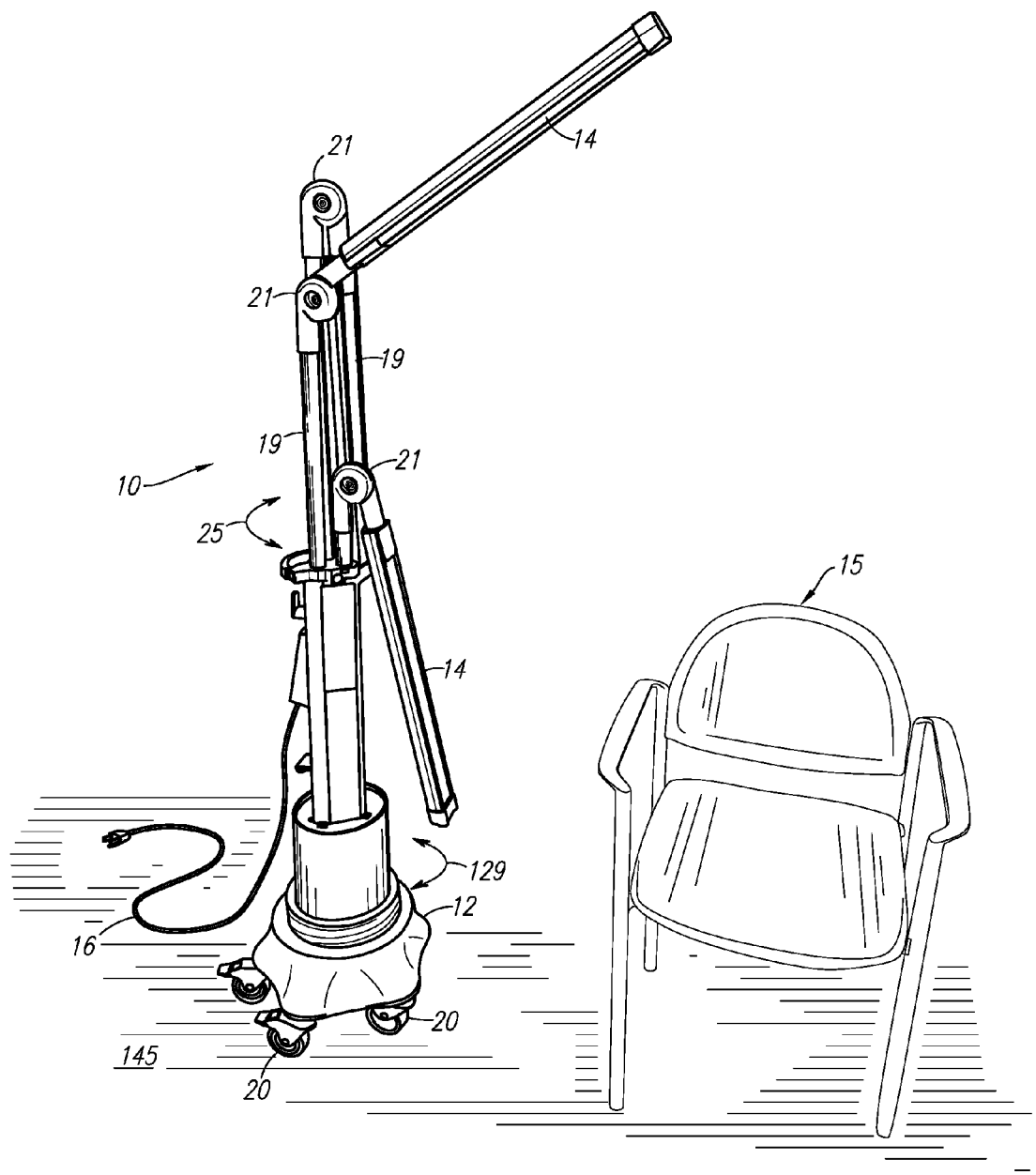
FIG. 5 shows a perspective view of an autonomously-movable decontamination apparatus.
Figure 6:
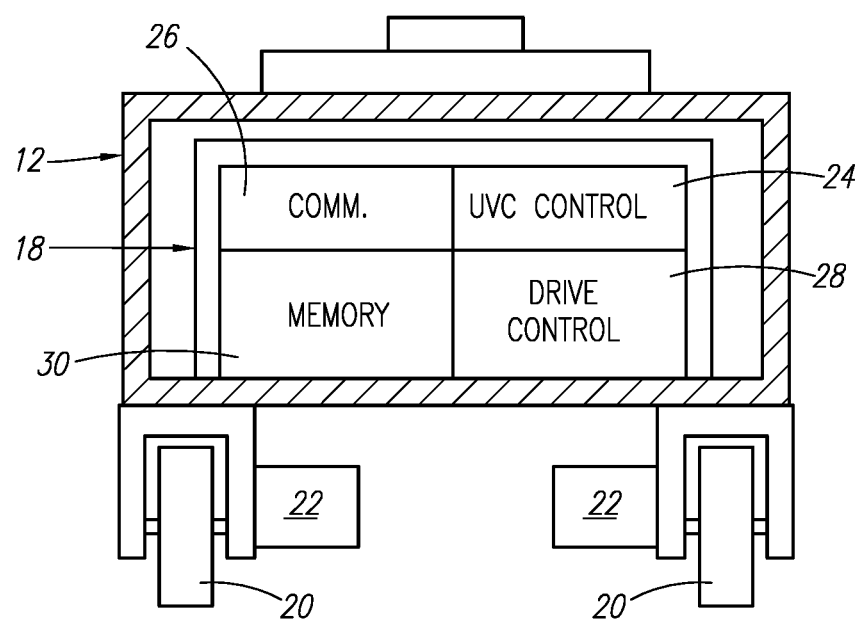
FIG. 6 shows a partially-cutaway view of a motorized base of the decontamination apparatus shown in FIG. 5.
Figure 7:
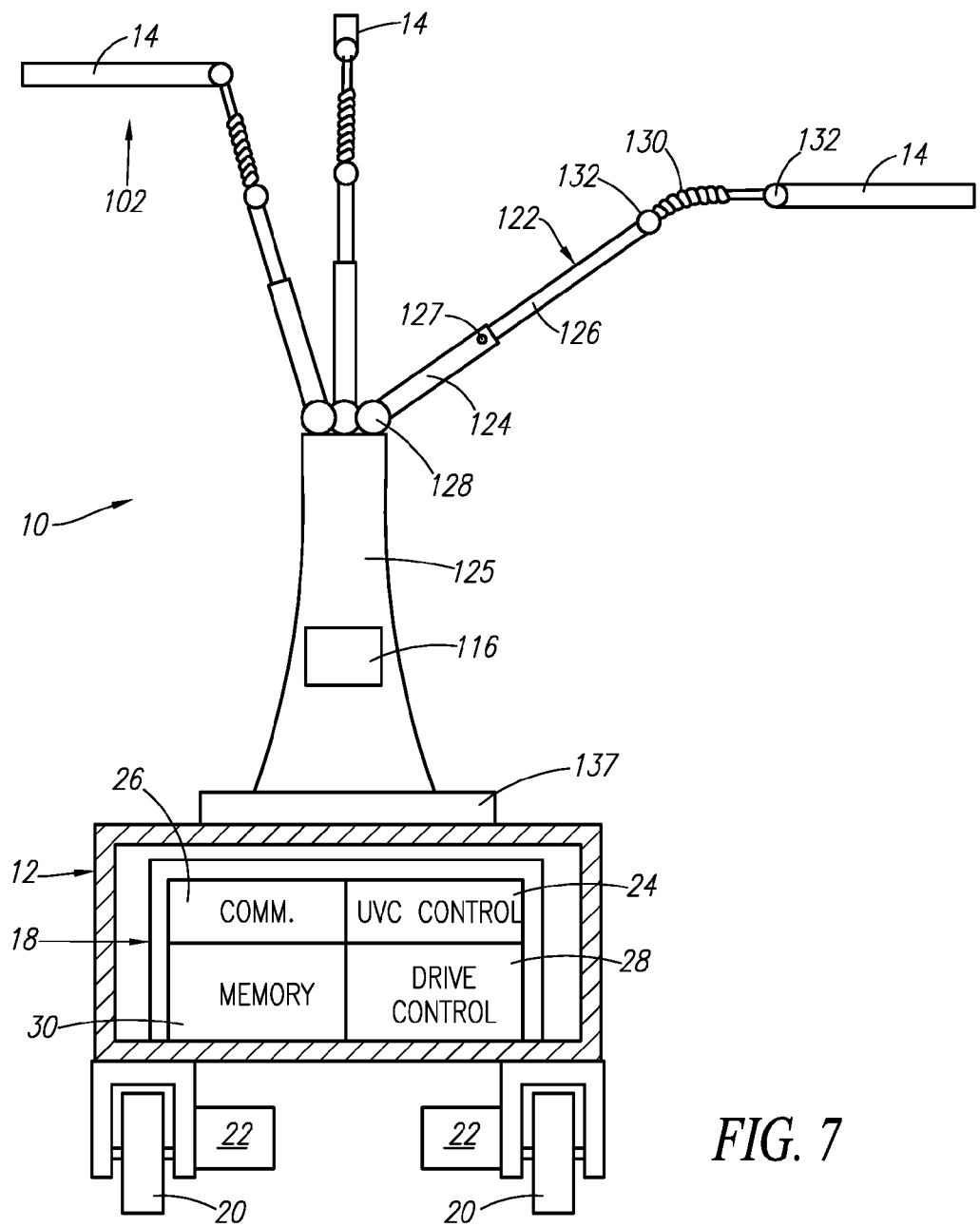
FIG. 7 shows an embodiment of a decontamination apparatus comprising a plurality of independently-adjustable UVC bulbs supported by a motorized base.

According to alternate embodiments, the decontamination apparatus 10 can be mobile, autonomously transported to a plurality of different locations along a programmed route within a room by a motorized base 12, as shown in FIGS. 5-7, without feedback or other information from the UVC sensors influencing movement of the decontamination apparatus 10. Transporting the decontamination apparatus 10 as described herein allows for the decontamination apparatus 10 to expose surfaces (e.g., chair 15 in FIG. 5) to UVC light while the decontamination apparatus 10 is at one location, and such surfaces are shielded from the UVC light emitted by the decontamination apparatus 10 by a shroud 17 (FIG. 8) provided adjacent to the UVC lights 14 at a first location (e.g., where the decontamination apparatus 10 is initially activated). For such embodiments, the velocity at which the decontamination apparatus 10 moves can be set slow enough to ensure all surfaces desired to be irradiated and rendered pathogen reduced along the way receive a dose of UVC light suitable to achieve at least a predetermined level of pathogen reduction. In this manner, the UVC light can be focused on the surfaces of interest, delivering an intense dose to achieve the desired level of pathogen reduction without necessarily requiring high-power UVC lights that broadcast UVC light indiscriminately within the room. Transporting the decontamination apparatus 10 to a plurality of different locations throughout the room allows for the UVC-emitting bulbs 14 to be positioned within close proximity (e.g., within five (5) feet, or optionally within four (4) feet, or optionally within three (3) feet, or optionally within two (2) feet, or optionally within one (1) foot) to the surfaces being decontaminated. Thus, a plurality of UVC-emitting bulbs 14 that are relatively low power (e.g., unable to achieve a desired level of pathogen reduction such as a 1 $\log_{10}$ reduction on the surfaces in under ten (10) minutes when separated from the surfaces by at least three (3) feet), can be included as part of the decontamination apparatus 10 instead of a central, high-power UVC bulb that broadcasts UVC light from a single location within the room to achieve pathogen reduction.

As shown in FIG. 5, the decontamination apparatus 10 is not stationary, but mobile. The decontamination apparatus 10 includes at least one, and optionally a plurality of vertically-oriented and/or adjustable UVC-emitting bulbs 14 extending upwardly from the base 12. As shown in FIG. 5, the UVC bulbs 14 are supported, individually or in groups of two or more, adjacent to a distal end of a plurality of adjustable arms 19. Each arm 19 includes a hinge 21 or other adjustable joint that allows the respective arm 19 to be articulated, adjustable in length or a combination thereof that allows the position and/or orientation of the UVC bulbs 14 to be adjusted. Each arm 19 can also optionally be rotatable about a longitudinal axis of the segment extending vertically upward from the base 12, in directions indicated generally by arrow 25.

An electric cord 16 is configured to be plugged at one end into a conventional AC mains wall outlet supplied with electric energy from a public utility, for example, and is operatively connected to conduct electric energy from the outlet to a controller 18 (schematically shown in FIG. 6) disposed within the base 12. A plurality of wheels 20 are coupled to the underside of the base 12, allowing the base 12, and accordingly the Decontamination apparatus 10, to be rolled along the surface of a floor. At least one, and optionally a plurality of the wheels 20 can optionally be pivotally coupled to the underside of the base 12 to allow the decontamination apparatus 10 to be rolled around corners and otherwise change directions of travel. At least one, and optionally a plurality of the wheels 20 can optionally be arranged in a fixed orientation relative to the base 12, and be drive by a motor 22 as described below. At least one, and optionally a plurality of the other wheels 20 can be pivotally coupled to the base 12. For such embodiments, one, but less then all of the motor-driven wheels can be operated at a speed different than at least one other motor-driven wheel, causing the pivotal wheel(s) 20 to turn, allowing the base 12 to turn and move in a variable direction. According to yet other embodiments, the wheels 20 can optionally be replaced by any suitable transportation devices such as one or a plurality of motor-driven tracks that include a belt that travels over a plurality of wheels, allowing the base 12 to be skid steered, for example. However, for the sake of brevity and clarity, the embodiments utilizing wheels 20 to transport the base 12 will be described in detail.

As shown in FIG. 7, the decontamination apparatus 10 includes a plurality of (three) independently-positionable sources including one or a plurality of UVC bulbs 14 that each direct UVC light toward the surface(s) to be rendered pathogen reduced. The UVC bulbs 14 are said to be independently positionable in that the position of each can be adjusted and maintained relative to the other UVC bulb(s) 14. Such a decontamination apparatus 10 can also optionally include an occupant sensor that determines whether the room 1 is occupied or not, and a controller 116 that interferes with emission of the UVC light if the room 1 is, or becomes occupied based on a signal from the occupant sensing system.

Figure 8:
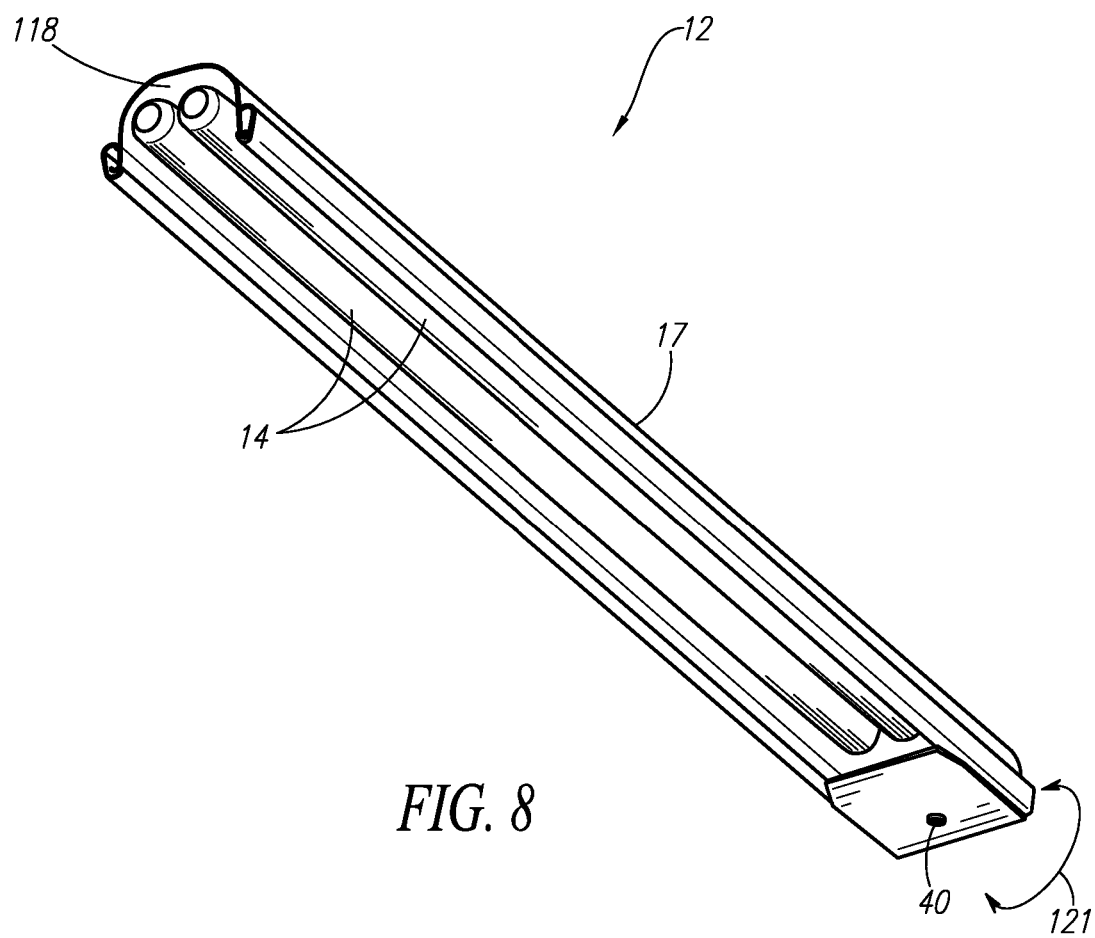
FIG. 8 shows a perspective view of one set of UVC bulbs shown in FIG. 7.

From the viewpoint illustrated in FIG. 8 looking up into a pair of parallel bulbs 14 in the direction indicated by arrow 102 in FIG. 7, the bulb(s) 14 are coupled to a reflective shield 118 provided to an inward-facing surface of the shroud 17 that focuses the UVC light toward the surface(s) 15 being decontaminated. The bulb 14 and/or reflective shield 118 can be pivotally coupled to a distal end of an articulated arm 122 or other suitable support that allows the bulbs 14 and/or shield 118, to be pivoted about a rotational axis in the directions indicated by arrow 121 and otherwise positioned in a suitable position relative to the surface to achieve the desired level of decontamination within a predetermined period of time (e.g., less than ten (10) minutes, less than eight (8) minutes, less than six (6) minutes, less than 4 (4) minutes, less than three (3) minutes, etc.), once activated. The parallel bulbs 14 provided with a common shield 118 are independently positionable relative to the bulb(s) 14 supported by the other arm(s) 122. An example of such repositionable bulbs is described in U.S. Pat. No. 9,095,633 to Dayton, which is incorporated in its entirety herein by reference.

According to the embodiment in FIG. 7, each arm 122 can include a portion including an adjustable length extending generally away from a base portion 125, which can be facilitated by an external member 124 that telescopically receives an internal member 126, or other suitable length adjustment mechanism (e.g., sliding track, etc. . . . ). A locking member 127 such as a spring-biased pin urged toward a locking position, detent, etc. . . . can be provided to one or both of the external and internal members 124, 126 to maintain a desired length of the arm 122, once manually established. A hinge 128 or other connector suitable to allow angular adjustment of the arm 122 relative to the base 125 can be disposed between the base 125 and the arm 122. A bendable joint 130 can also optionally be provided anywhere along the length of the arm 122, such as adjacent to the distal end of the arm 122 where the bulb(s) 14 is/are supported. The joint 130 can be formed from a plastically-deformable flexible material that can be manually bent to position the bulb(s) 14, yet be sufficiently rigid to maintain the position of the housing relative to the arm 122 once the bending force has been removed. Further, a hinge 132 can also optionally be positioned along the arm 122 before and/or after the joint 130 to allow further adjustment of the position of the bulb(s) 14 to achieve the desired coverage of the surface to be decontaminated with UVC light. As with any of the hinges described herein, the hinge(s) 132 can be selectively lockable, meaning a locking member such as a set screw, for example, can be loosened to allow the structures coupled to opposite sides of the hinge(s) 132 to be pivotally adjusted relative to each other. Once the desired adjustment has been completed, the set screw or other locking member can be tightened to interfere with further pivotal adjustment of the structures relative to each other.

The base 125 supports the arms 122 at a desired elevation above the floor of the room, and can optionally be mounted on an adjustable platform 137 that rotates about a vertical axis in directions generally indicated by arrow 129 in FIG. 5. The base 125 supports a controller 116 that can be manipulated by a user to control operation of the decontamination apparatus 10 (e.g., independently control operation of each bulb 14 to emit UVC light, optionally to cause one bulb 14 to remain energized longer than another one of the bulbs 14), and optionally houses an on-board power supply such as a rechargeable battery bank or circuitry for utilizing electricity from an AC mains source such as a wall outlet supplied by an electric utility that can be used to energize the bulbs 14 and power the controller 116. A power cord 16 can be plugged into an AC mains electric outlet supplied by an electric power utility to obtain the electric energy needed to power the decontamination apparatus 10.

Regardless of the embodiment of the decontamination apparatus 10, at least one, and optionally each of the plurality of wheels 20 can be driven by an electric motor 22 to allow the decontamination apparatus 10 to travel autonomously, without the direct assistance of a human user while the decontamination apparatus 10 is underway. In other words, the decontamination apparatus 10 can navigate along a path in a plurality of different directions, between a plurality of waypoints, in a room being decontaminated to render that room pathogen reduced without being physically contacted by a human user to steer the decontamination apparatus 10 during the decontamination process, and optionally without receiving remote control signals being manually input in real-time by a human operator.

To be rendered "pathogen reduced", at least a portion, optionally less than all, of a biologically-active present on the exposed surface of objects exposed to the UVC light emitted by the UVC bulb(s) 14 is deactivated. For instance, rendering objects in a room pathogen reduced does not necessarily require those objects to be made 100% sterile, free of any and all biologically-active organisms that can viably infect a human being. Instead, being rendered pathogen reduced requires a lower level of biologically-active contagions viable to cause an infection to remain on the surface of the objects after performance of the decontamination process herein than existed on those surfaces prior to performance of the decontamination process. Also, deactivation of the biologically-active contagions can include killing live contagions, or at least neutralizing their ability (e.g., rendering them no longer viable) to reproduce to an extent that results in an infection in a human exposed to the deactivated contagions.

According to other embodiments, decontaminated surfaces can be required to possess a lower level of viable or otherwise biologically-active contagions than a threshold quantity permitted under U.S. Food and Drug Administration requirements on objects dedicated for use in a sterile field such as in an operating room during a surgical procedure. According to other embodiments, the decontamination process can be required to kill or otherwise deactivate at least 99% of all living or otherwise biologically-active contagions present on the exposed surfaces immediately prior to performance of the decontamination process to render those surfaces pathogen reduced.

According to yet other embodiments, achieving pathogen reduction amounting to a high-level disinfection of the surfaces in the room utilizing the decontamination apparatus 10 can involve deactivation of a suitable portion of the biologically-active contagions to achieve at least a 1 $\log_{10}$ reduction of viable contagions on the object that remain infectious (i.e., no more than $\frac{1}{10}$th of the biologically-active contagions originally present remain active or infectious at a time when the decontamination process is completed). According to yet other embodiments, achieving high-level disinfection of the surfaces utilizing the decontamination apparatus 10 can involve deactivation of a suitable portion of the biologically-active contagions to achieve at least a 3 $\log_{10}$ reduction (i.e., $\frac{1}{1,000}$th) of viable contagions originally present on the surfaces exposed to UVC light. According to yet other embodiments, achieving high-level disinfection of such surfaces can involve deactivation of a suitable portion of the biologically-active contagions to achieve at least a 5 $\log_{10}$ reduction (i.e., $\frac{1}{100,000}$th) of viable contagions thereon.

As shown in FIG. 6, an independently-controllable electric motor 22 is provided to each of the wheels 20, however alternate embodiments can include a plurality of wheels 20 driven by a common electric motor 22 through the use of a drivetrain (not shown). Yet other embodiments can include a steering mechanism (not shown) for controlling a direction in which the decontamination apparatus 10 travels, that allows fewer than all of the wheels 20 to be driven by a motor. But for purposes of this disclosure, each of the wheels 20 is driven such that the direction in which the decontamination apparatus 10 travels can be controlled by selectively controlling operation of each of the motors 22 individually, at different speeds. Thus, when a first motor 22 is operated to drive its respective wheel at one speed, and a second motor 22 on an opposite side of the base 12 drives its respective wheel at a faster speed, then the decontamination apparatus 10 is caused to turn toward the slower-driven wheel 20.

A schematic representation of the controller 18 is shown in FIG. 6. For the illustrated embodiment, the controller 18 includes a UVC control component 24 that selectively controls the delivery of electric energy supplied via the power cord 16 to the UVC-emitting bulb(s) 14. The UVC control component 24 can include a timer that, upon expiration of a predetermined period of time, which can optionally be manually specified by a user, causes deactivation of the UVC-emitting bulb(s) 14.

According to alternate embodiments, one or more of the UVC sensors described above can optionally communicate, in real-time with an optional communication component 26 provided to the controller 18 to limit the duration of a decontamination process during which the UVC-emitting bulb(s) 14 is/are activated. For example, a plurality of the UVC sensors can be arranged in a room that is to be decontaminated utilizing the decontamination apparatus 10. The decontamination apparatus 10 can be placed in the same room and activated in a mode that maintains operation of the UVC bulb(s) 14 until all of the UVC sensors therein have been exposed to a threshold minimum level of UVC light emitted by the Decontamination apparatus 10. Each UVC sensor measures the extent of UVC exposure and, in response to sensing exposure to the minimum level of UVC light, transmits a wireless signal to be received by the communication component 26. Once all of the UVC sensors have transmitted such a signal indicating adequate exposure to UVC light for the decontamination process and the signals are received by the communication component 26, the communication component 26 transmits a signal to the UVC control component 24 which, in turn, deactivates the UVC bulb(s) 14.

Alternate embodiments of the communication component 26 can optionally receive signals that are used to control relocation of the decontamination apparatus 10 using the wheels 20, as described below. For instance, the UVC sensors described above as being distributed throughout a room can optionally emit signals indicative of the level of UVC light to which those UVC sensors have been exposed. Such signals can be received by the communication component 26 and utilized by the communication component 26 to determine whether there are UVC sensors within the room that have not been exposed to a sufficient level of UVC light to achieve the desired level of decontamination within regions adjacent to the UVC sensors. Based, at least in part on such a determination, the decontamination apparatus 10 can remain within close proximity to the insufficiently-exposed UVC sensors until those sensors have been exposed to a suitable level of UVC light to achieve the desired level of decontamination before proceeding to a subsequent location.

According to alternate embodiments, the controller 18 can also include a drive control component 28 that controls operation of the electric motor(s) 22 driving the wheels 20 based on a plurality of waypoints stored by a computer-readable memory forming a portion of a memory component 30. Each waypoint establishes a location within a room or other environment where the decontamination apparatus 10 is to arrive autonomously as part of its journey during a decontamination process. The waypoints can optionally be saved by the memory component to reflect a generic pattern common to a plurality of patient rooms within a hospital, guest rooms in a hotel, or other commonly-configured locations. Thus, the decontamination apparatus 10 can be placed at a starting point common to each such room, and optionally labeled in each such room, and activated in a decontamination mode that calls for the decontamination apparatus 10 to travel to each waypoint autonomously to complete the decontamination process. Once the decontamination process is complete in one such commonly-configured room, the decontamination apparatus 10 can be manually transported to the next commonly-configured room, placed at the starting point and reactivated in that mode to also decontaminate that room. This process can be repeated for each such commonly-configured room to be decontaminated. The memory component 30 can optionally store different waypoints for different room configurations, allowing an operator to press a button specific to a given room to cause the decontamination apparatus 10 to autonomously navigate the waypoints specific to the button that was pressed.

Figure 9:
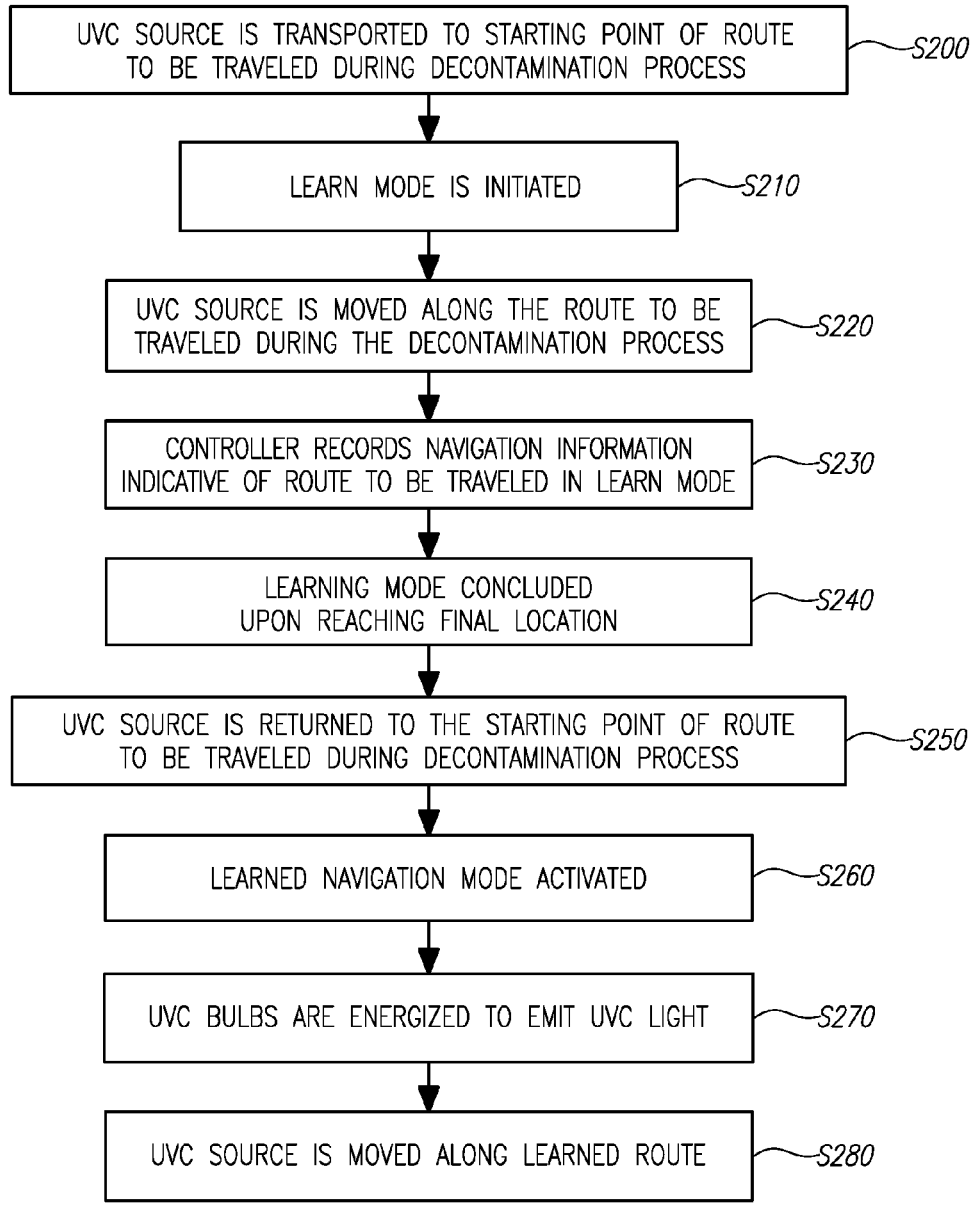
FIG. 9 shows a flow diagram schematically illustrating a method of performing a decontamination process.

According to other embodiments, the decontamination apparatus 10 can be placed in a "learn" mode to allow an operator to manually enter the desired waypoints for a specific room into the memory component 30. In use, as illustrated by the flow diagram of FIG. 9, the operator of the present embodiment can manually transport (e.g., push or otherwise directly control) the decontamination apparatus 10 to the starting point of a route to be navigated by the decontamination apparatus 10 to complete a decontamination process at step S200. Once at the starting point, the operator can cause the decontamination apparatus 10 to enter the learn mode at step S210 via an appropriate user interface, and then manually move the Decontamination apparatus 10, at step S220, along the route to be autonomously traveled by the decontamination apparatus 10 with the UVC-emitting bulb(s) 14 energized after the operator has left the room. The drive control 28 can include one or more sensors that can be used to sense signals indicative of a heading (e.g., angular pivoting of the wheels 20 to determine a direction relative to the starting point) and the distance traveled (e.g., a timer that determines the duration for which the motor 22 would be operational to travel between waypoints) until the final location is reached, as manually indicated by the operator. This navigation information can be recorded by the controller 18 at step S230.

Upon reaching the final location to which the decontamination apparatus 10 will travel as part of the decontamination process, the operator can identify this location by terminating the learn mode via an appropriate user interface at step S240. To conduct the decontamination process, the operator can manually return the decontamination apparatus 10 to the starting point at step S250, optionally arrange one or a plurality of UVC sensors throughout the room at desired locations to ensure a thorough decontamination, and initiate the decontamination process at step S260 by selecting the learned navigation mode via an appropriate user interface. Following the expiration of a predetermined period of time sufficient to allow the operator to exit the room and close the door, the UVC control component 24 activates the UVC-emitting bulb(s) 14 at step S270. Once the desired level of decontamination has been achieved on the surfaces within the room exposed to the UVC light emitted by the UVC bulb(s) 14 with the decontamination apparatus 10 in the starting point, the drive control component 28 controls operation of the motor(s) 22 to move the decontamination apparatus 10 along the route learned in the learn mode at step S280. Again, movement of the decontamination apparatus 10 can optionally be influenced by, or independent from feedback from one or more of the UVC sensors in the room and received by the communication component 26, by a timer (e.g., after remaining at the starting point for a predetermined period of time, move onward), and/or any other factor indicative of a level of decontamination of surfaces near the starting point. The decontamination apparatus 10 can utilize GPS navigational triangulation, a timer and directional sensor to activate the motor(s) 22 for known lengths of time in certain directions, and any other control factors during autonomous transportation of the decontamination apparatus 10 along the learned (or preprogrammed) route. The rate at which the decontamination apparatus 10 travels can be sufficient to achieve the desired level of decontamination as the decontamination apparatus 10 moves, and/or the decontamination apparatus 10 can stop at one, a plurality or all of the waypoints learned in the learn mode to achieve the desired level of decontamination of the exposed surfaces. Upon reaching the final destination for that learned route, the UVC bulbs are de-energized to complete the decontamination process.

Instead of returning the decontamination apparatus 10 to the start point where the learn mode was initiated at step S210 to prepare the decontamination apparatus 10 to proceed along the learned route, the decontamination apparatus 10 can optionally remain at the final location where the learn mode was concluded at step S240. According to the present embodiment, the learned navigation mode can be activated while the decontamination apparatus 10 is at this location (i.e., without returning the decontamination apparatus 10 to where the learn mode was initiated), and the decontamination apparatus 10 will travel along the learned route in reverse. In other words, the decontamination apparatus 10 will begin operating in the learned navigation mode at step S260, the UVC bulbs will be energized at step S270, but the decontamination apparatus 10 travels backwards along the learned route from the final location where the learn mode was concluded at step S240 toward the starting point where the learn mode was initiated at step S210. Thus, the need to manually return the decontamination apparatus 10 to the original starting point of the route can be avoided.

According to alternate embodiments, hospital rooms, hotel rooms, etc., can optionally be provided with one or more markings on the floor (e.g., a stripe of reflective material, dots of paint, etc. . . . ) that can be sensed by a sensor provided to the underside of the base 12. The sensor can be operationally connected to communicate directional signals to the drive control component 28 to cause selective operation of the motor(s) 22 as appropriate to cause the decontamination apparatus 10 to follow the path defined by the markings on the floor. According to such embodiments, the markings can eliminate the need to pre-program waypoints into the memory component 30, instead allowing the decontamination apparatus 10 to simply follow the markings along a desired path.

Figure 10:
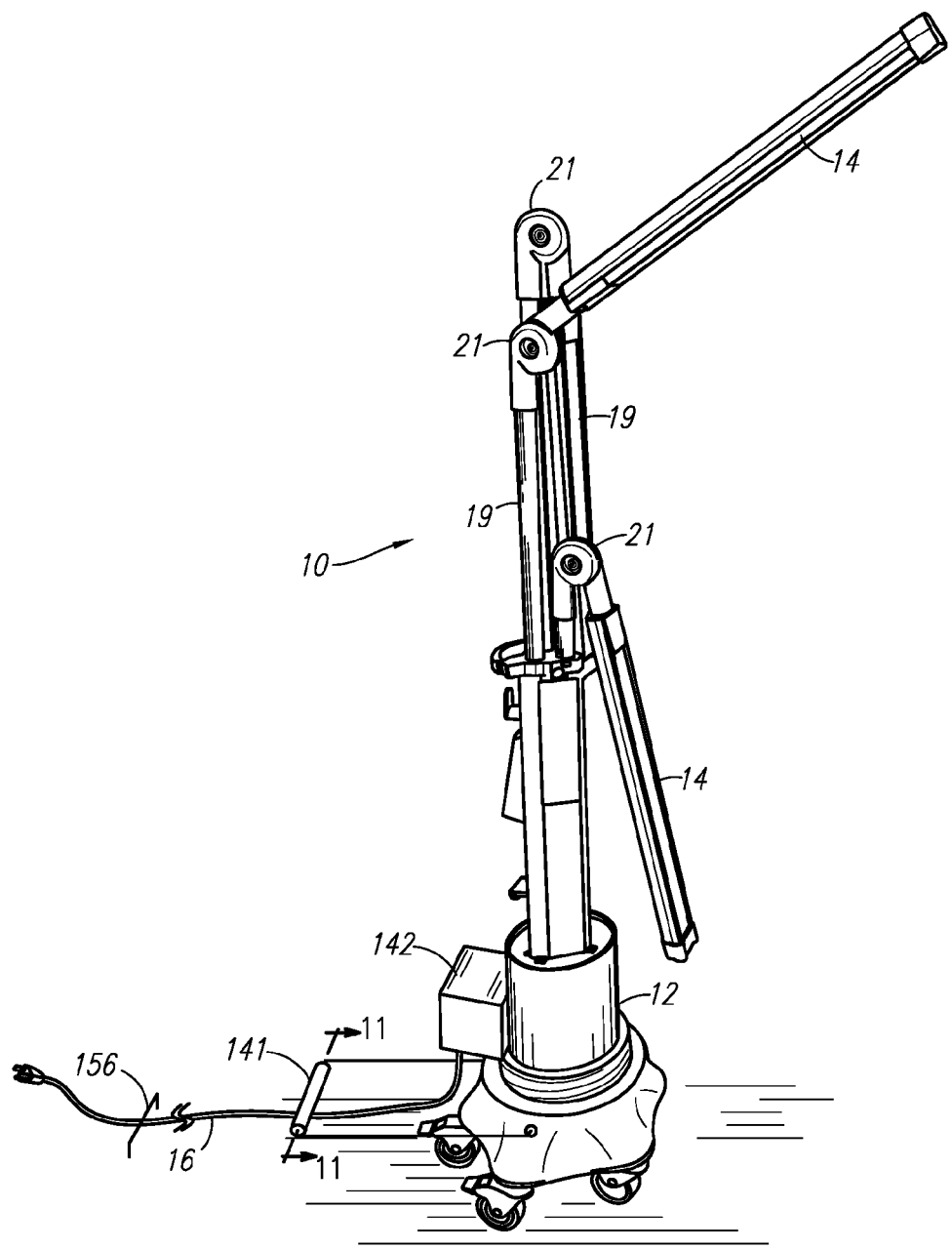
FIG. 10 shows a perspective view of an alternate embodiment of an autonomously-movable decontamination apparatus including a forward-mounted spool.
Figure 14:
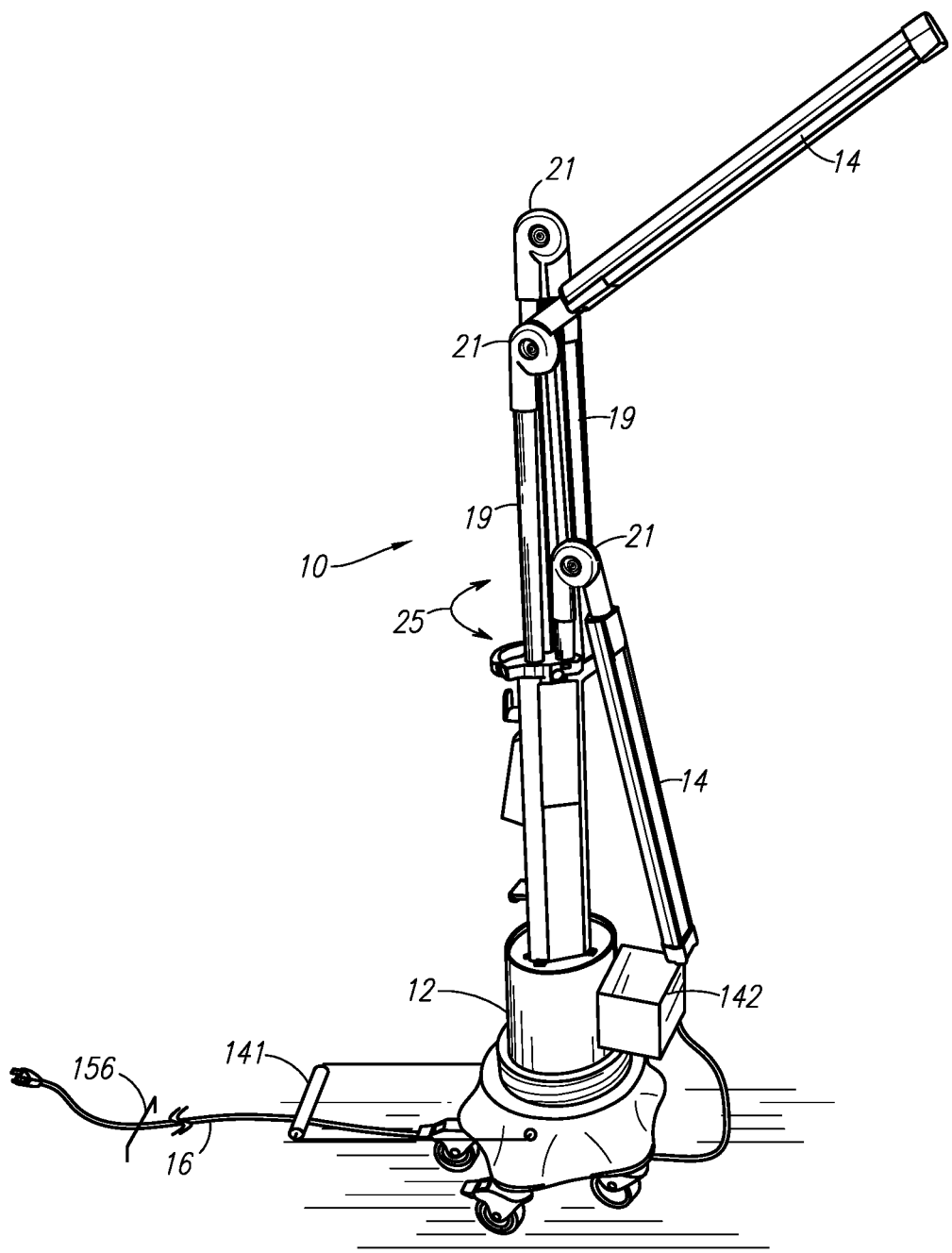
FIG. 14 shows a perspective view of an alternate embodiment of an autonomously-movable decontamination apparatus including a rearward-mounted spool.

Yet another embodiment of the decontamination apparatus 10 is shown in FIG. 10. According to the present embodiment, the base 12 also includes a line sensor 141 that can sense colors, and transmit signals distinguishing between different colors that are sensed. The line sensor 141 can optionally be supported by a pivotal arm 144 to support the line sensor 141 a sufficient distance in front of the base 12 to allow the base 12 to follow the cord 16, and optionally be pivoted about a pivot point 146 to an upright orientation relative to the base 12 when not in use. The electric cord 16 can include a flexible sheath that allows a portion of the cord 16 to be moved without disturbing another section of the cord 16 within at least two (2 ft.) feet of the portion that is moved. A spool 142 is operable to wind the cord 16 at approximately the same rate as the base 12 travels along a route following the cord 16. Depending on factors such as the material used to form the sheathing of the cord 16, the wire gauge of the electrical conductor within the cord 16, and other such factors, the cord 16 can be plastically deformed to include a "kink," "crimp" or other deformation of the cord's original linear shape. For embodiments where the base 12 is traveling along a route defined by the layout of the cord 16, such deformations can cause the base 12 to travel in undesired directions reflecting the deformed shape of the cord 16. In an effort to avoid, or at least mitigate formation of such deformations of the cord 16 to an extent that causes the base 12 to deviate laterally by more than at least two inches, or at least four inches, or at least six inches, or at least 8 inches, etc., from a desired straight line route defined by the cord 16, the externally-exposed material enclosing the electrical conductor(s) can optionally be made of vinyl with suitable flexibility to be wound by a spool having a diameter of less than six (6 in.) inches without plastically deforming at room temperature. According to alternate embodiments, the vinyl sheath of the cord 16 can be suitably flexibility to be wound by a spool having a diameter of less than five (5 in.) inches, or less than five (4 in.) inches without plastically deforming at room temperature to an extent that prevents the cord 16 from being deployed to define a substantially straight portion of a route along which the base 12 is to travel while following the cord 16. Although the spool 142 is shown in FIG. 10 as being arranged at the front of the motorized base 12 (i.e., forward of the motorized base 12 traveling along the cord 16), an alternate embodiment of the spool's location is shown in FIG. 14. According to that embodiment, the spool 142 is arranged at the rear of the motorized base 12 (i.e., behind the motorized base 12 traveling along the cord 16) to collect segments of the cord 16 after the motorized base 12 has traveled over those segments. It is believed that mounting the spool 142 at the rear of the motorized base 12 will cause less movement of the segment of the cord 16 arranged on the floor near the line sensor 141 as the spool 142 collects the cord 16.

The cord 16 can also optionally include an electrical conductor of suitable gauge to supply the electric current required to energize the UVC bulbs 14 and the motors and/or controllers to transport the base 12 along the cord 16, yet not be of such a low gauge (i.e., large diameter) that interferes with arrangement of the cord 16 on the floor 145 (FIG. 5). For example, the cord 16 can include a stranded set of wires or other suitable electrically-conductive material as low as 14 gauge, or as low as 16 gauge, or as low as 18 gauge, etc., without departing from the scope of the present disclosure.

Figure 12:
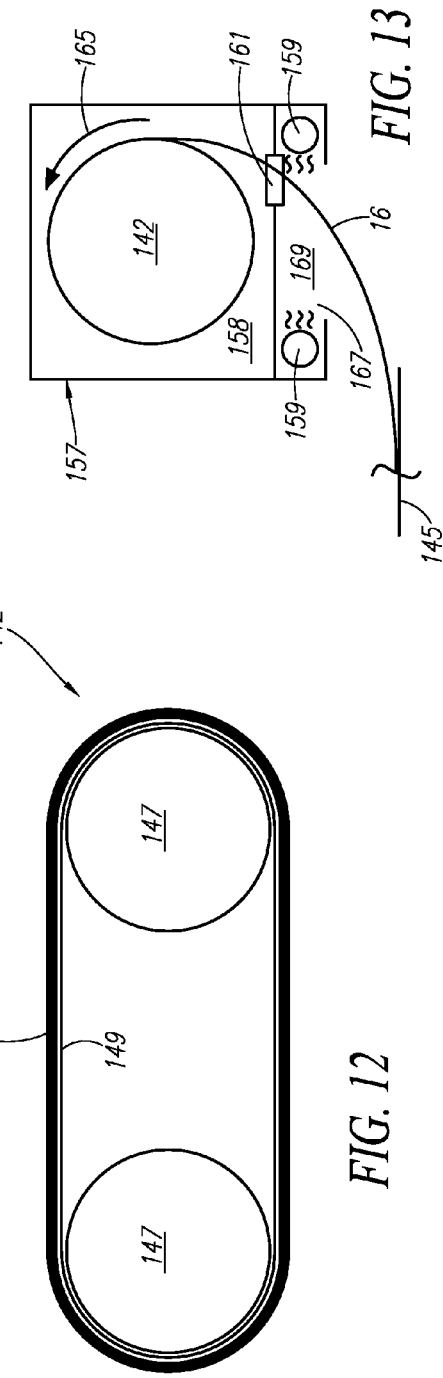
FIG. 12 shows an alternate embodiment of a spool for collecting a cord.

According to alternate embodiments, the spool 142 about which the cord 16 is to be wound when collected can optionally have a suitably large diameter to avoid forming kinks or other plastic deformation of the cord 16 as a result of prolonged storage at room temperature. Such a spool 142 can be used with or without the flexible cord that resists plastic deformation described above, and can be configured to collect and store cords 16 having lengths of at least twenty five (25 ft.) feet, and optionally at least thirty five (55 ft.) feet, at least fifty (50 ft.) feet, or optionally up to one hundred (100 ft.) feet. For example, the spool 142 about which the cord 16 is to be wound can optionally have a round cross-sectional shape, and be at least one (1 ft.) foot in diameter, or at least six (6 in.) inches in diameter, or at least three (3 in.) inches in diameter. According to alternate embodiments, the spool 142 can include a plurality of round hubs 147 (FIG. 12) about which a belt 149 can extend to form a generally-oval shaped spool 142 about which the cord 16 is to be wound. Any desired configuration of the spool 142 that avoids plastic deformation of the cord 16 when deployed as described below to define the route can be utilized without departing from the scope of the present disclosure.

The winding rate of the spool 142 can be variable based on the speed of the motor-driven wheel(s) 20, as determined based on a signal from the drive control 28 shown in FIG. 7, based on a sensed rate of travel based on a signal from the line sensor 141, based on a calculated rate at which the base 12 is traveling from GPS signals, or based on any other sensed or calculated value indicative of the rate at which the base 12 is moving along the cord 16. The rate at which the base 12 is turning or changing direction as determined based on the sensed layout of the cord 16 can also be factored into the rate at which the spool 142 is rotated to pick up the cord 16. For example, the base 12 can be configured to travel at a rate along the cord 16 that ensures exposure of the surfaces being exposed to, and decontaminated by the UVC light emitted by the UVC bulbs 14 receives a suitably dose of UVC light to achieve the desired level of pathogen reduction. Specific examples of the rates the base 12 can travel along the cord 16 include rates that ensure the specific surfaces being decontaminated are exposed to a suitable intensity of UVC light for at least thirty (30 sec.) seconds, or at least sixty (60 sec) seconds, or at least ninety (90 sec.) seconds, etc. to achieve the desired level of pathogen reduction.

Figure 13:
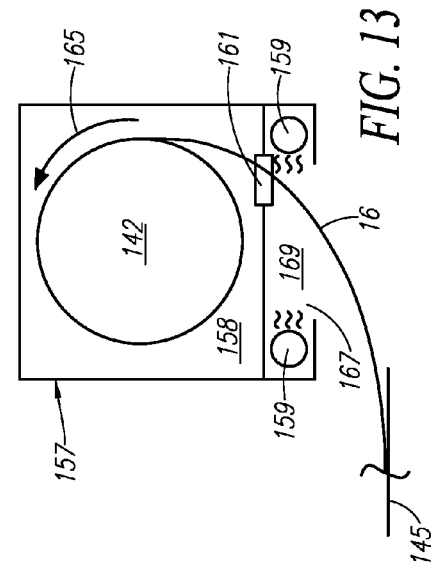
FIG. 13 shows an embodiment of a housing enclosing a spool that collects a cord in a decontaminated state from an underlying floor.

Regardless of the dimensions of the spool 142 and configuration of the cord 16, the spool 142 can optionally include a housing 157 that substantially encloses at least one, and optionally a plurality of UVC bulbs 159, as shown in FIG. 13, which emit(s) UVC light to decontaminate the cord 16 as it is being collected from the underlying floor 145 by the spool 142 as the base 12 travels along the length of the cord 16. For the illustrated embodiment, the housing 157 defines an interior space 158 in which the spool 142 is pivotally mounted to rotate in a counterclockwise direction (indicated generally by arrow 165) in the perspective of FIG. 13 to collect the cord 16, and in a clockwise direction in the perspective of FIG. 13 to allow the cord 16 to be deployed from the spool 142. The housing defines an aperture 167 through which the cord 16 enters the housing 157, and a vestibule chamber 169 in which the one or more UVC bulbs 159 are disposed. According to the embodiment shown in FIG. 13, the UVC bulbs 159 are arranged in the vestibule chamber 169 such that a portion of the housing 157 separates the UVC bulbs 159 from the underlying floor 145 to protect the UVC bulbs 159 against being impacted from below the base 12. However, alternate embodiments can optionally include UVC bulbs 159 that are arranged at an elevation vertically beneath the interior space 158 to emit UVC light that impinges on the cord 16 as it is lifted from the floor 145 and wrapped around the spool 142. These UVC bulbs 159 can be exposed to the floor 145 (e.g., unprotected by a portion of the housing 157 or other shield), or optionally shielded from below by a UVC transparent material that allows the UVC light from the UVC bulbs 159 to impinge on the floor 145 as the base 12 travels along the route defined by the cord 16 or along the route as learned or otherwise established elsewhere herein during a decontamination process. According to such alternate embodiments, the UVC light emitted by the UVC bulbs 159 can also optionally achieve the desired level of pathogen reduction on the floor 145 as the base 12 travels. However, for embodiments where the base 12 follows the route defined by the cord 16, the UVC light emitted by the UVC bulbs 159 achieve the desired level of pathogen reduction on the exposed surfaces of portions of the cord 16 as those portions travel between the floor 145 and the interior space 158. In other words, the portion of the cord 16 that has been elevated off the floor 145 but has not yet entered the interior space 158 will be rendered pathogen reduced as a result of being exposed to the UVC light from the UVC bulbs 159.

UVC light can negatively affect the integrity of the exposed surfaces of the cord 16 that are continuously exposed to UVC light for prolonged periods of time. To protect against such prolonged exposure of the cord 16 to UVC light, the housing 157 can also include a light shield 161 that is substantially opaque to UVC light. The light shield 161 interferes with the transmission of the UVC light from the UVC bulbs 159 into the interior space 158, where the cord 16 is stored on the spool 142, yet allows the cord 16 to enter the interior space 158 while being collected. Illustrative embodiments of the light shield 161 include opposing bristles that extend a sufficient distance from opposing surfaces to overlap each other within the aperture through which the cord 16 enters the interior space 158. The cord 16 can temporarily deform such bristles to enter the interior space 158, yet the bristles conform sufficiently to block a majority (e.g., at least 50%, or at least 60%, or at least 70%, or at least 80%, or at least 90%, etc.) of the UVC light from the UVC bulbs 159 from entering the interior space 158. Alternate embodiments of the light shield 161 can include a flexible and/or deformable membrane defining an aperture with dimensions that tightly conform to the external shape of the cord 16 that extends across the aperture through which the cord 16 enters the interior space 158. However, any structure suitable to allow the cord 16 to enter the interior space 158 while interfering with the entrance of UVC light from the UVC bulbs 159 into the interior space 158 can be utilized.

The externally-visible color of the cord 16 can be any desired color that does not match the color of the underlying floor 145 (FIG. 5) on which the cord 16 is to rest to define the route along which the base 12 is to travel as described herein. In use, the cord 16 is removed from the spool 142 and plugged into the AC mains wall outlet in the room to be disinfected. The portion of the cord 16 between the base 12 and the wall outlet can be arranged on the floor 145 to define the route along which the base 12 is to navigate. Any excess length of cord 16 removed from the spool 142 can be retracted by the spool 142, or accumulated near the wall outlet to mark the end of the route. A marker 156 of a color, configuration or other property that can be sensed by the line sensor 141 can optionally be deployed over a portion of the cord 16 arranged on the floor 145 to identify the end of the route.

Figure 11:
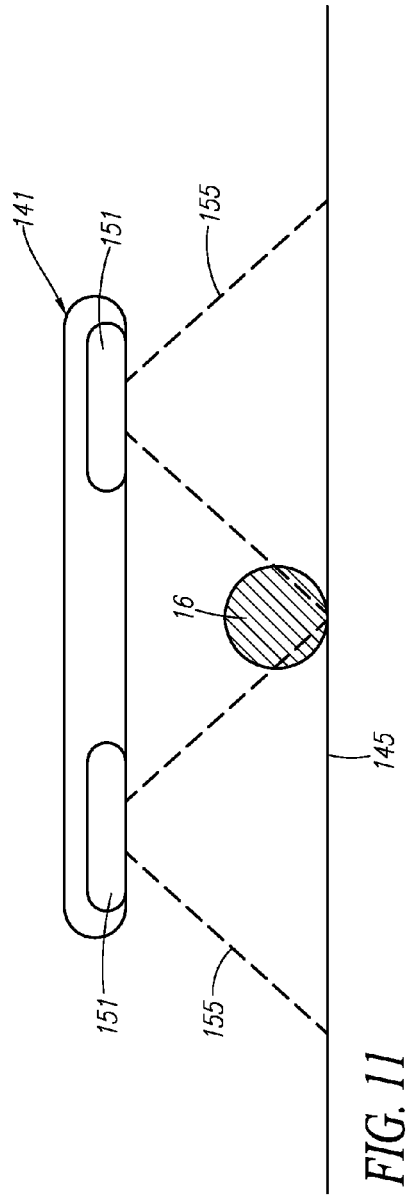
FIG. 11 shows a sectional view of an embodiment of a line sensor arranged to extend transversely across a cord on a floor.

The external color of the cord 16 can be a bright yellow, orange, or other suitable color that contrasts well with flooring commonly found in healthcare facilities or other environments where the decontamination apparatus 10 is to be used. As shown in FIG. 11, which is a sectional view of the line sensor 141 taken along line 11-11 in FIG. 10, the line sensor 141 can include a plurality of photo-eyes 151 oriented with a downward sensory direction, illustrated by broken lines 155. The photo-eyes 151 can sense a color of the underlying floor 145 on which the cord 16 is deployed, and transmit a signal indicative of the sensed color to the drive control component 28. The color of the floor can be sensed continuously, occasionally, or periodically, and the drive control component 28 can optionally determine an average color of the floor 145. As the base 12 moves forward over the cord 16 deployed on the floor 145, the signals received by the drive control component 28 averages the color of the floor 145 based on a plurality of values sensed by the photo-eyes 151. Since the color of the cord 16 contrasts with the color of the floor 145, an individual sensed color value based on the signal transmitted by one or more of the photo-eyes 151 indicates that the base 12 has begun to drift or otherwise deviate from the route defined by the cord 16 on the floor 145. The drive control component 28 can also determine which of the photo-eyes 151 transmitted such a signal and adjust the operation of one or more drive motors 22 to correct the direction in which the base 12 is traveling such that the color sensed by each of the photo-eyes 151 is indicative of the floor 145. Upon reaching the excess cord 16 near the wall outlet and/or the marker 156 as detected by the photo-eye(s) 151, the drive control component 28 terminates operation of the drive motor(s) 22 and the UVC controller 24 terminates operation of the UVC bulbs 14, thereby concluding the decontamination process along the route marked by the cord 16.

Although the line sensor 141 is described in detail herein as including photo-eyes 151 to detect and follow the cord 16, the present disclosure is not so limited. According to other embodiments, the line sensor 141 can include probes that extend downwardly, generally toward the floor 145 and are sensitive to contacts with the cord 16, for example. For such embodiments, the probes can include at least left and right probes, arranged at opposite lateral sides of the line sensor 141, and the cord 16 deployed on the floor. When the right probe contacts the cord 16, the base 12 can control the direction of the base to travel in a direction that separates the right probe from the cord 16, keeping the cord 16 disposed between the left and right probes. The left probe can operate similarly, but cause the base 12 to travel in the opposite direction to keep the cord 16 between the left and right probes.

Other embodiments of the line sensor 141 can include left and right ultrasonic sensors in place of, or in combination with the photo-eyes 151. Like the probe embodiment, each ultrasonic sensor can sense the proximity of the cord 16 relative to the respective ultrasonic sensor, and the base 12 can change directions in response to the cord 16 becoming too close to one of the ultrasonic sensors, and thereby too far from the other ultrasonic sensor. Accordingly, the base 12 can be driven to keep the cord 16 in a middle region between such sensors.

Another embodiment of the line sensor 141 can include one, a plurality, or an array of current sensors that senses an electric current being conducted through the electrical conductor(s) of the cord 16 to power the base 12 and/or UVC bulbs 14, 159. Based on the magnitude of the current sensed by each one of the current sensors, and the position of the respective sensors that sensed the current magnitude along a width of the line sensor 141, the position of a central region of the line sensor 141 relative to the longitudinal axis of the cord 16 can be determined, and a correction of the drive direction of the base 12 made to cause the base 12 to follow the cord 16.

According to yet other embodiments, instead of or in combination with the photo-eyes 151, the line sensor 141 can include a temperature sensor or a plurality of temperature sensors along a width of the line sensor 141 arranged substantially perpendicular across the longitudinal axis of the cord 16. The temperature sensor(s) can be sensitive enough to detect a thermal response of the cord 16 to conducting electricity during operation of the decontamination apparatus 10 as part of a decontamination process. Such a line sensor 141 can be configured to, along with the base 12, follow a thermal signature of the cord 16 conducting electricity relative to a thermal signature of the underlying floor 145. Although the specific structure and/or sensor for sensing the route defined by the cord 16 on the floor is described herein in detail as a photo-eye 151 for the sake of brevity and clearly describing the invention, it is to be understood that any suitable sensor and/or structure can be used in place of, or in addition to the photo-eyes 151 to cause the base 12 to follow the cord 16.

For any of the embodiments above where the decontamination apparatus 10 is mobile, the base 12 or other portion of the decontamination apparatus 10 (e.g., any portion of the arms 19, shroud 17, bulbs 14, etc.) can optionally be equipped with a proximity sensor that utilizes ultrasonic waves, optical sensors, etc. . . . to detect when any portion of the decontamination apparatus 10 approaches a foreign object (e.g., furniture in the room, medical equipment on the floor, etc. . . . ) and is about to make physical contact with that foreign object. The proximity sensor can be operatively connected to transmit a signal to the drive control component 28 which, in turn, can deactivate the motor(s) 22 and stop the decontamination apparatus 10 before the decontamination apparatus 10 actually makes contact with the foreign object. Impending contact with a foreign object can also optionally be grounds to deactivate the UVC-emitting bulb(s) 14, thereby prematurely terminating the decontamination process. Under such circumstances, the operator can optionally be informed of premature termination of the decontamination process by a visible and/or audible indicator provided to the Decontamination apparatus 10, via a remote control outside of the room being decontaminated in response to receiving a signal transmitted by the communication component 26, simply by the position of the decontamination apparatus 10 at the unexpected location where decontamination was prematurely terminated instead of at the known end of the route, or via any other indicator.

Illustrative embodiments have been described, hereinabove. It will be apparent to those skilled in the art that the above devices and methods may incorporate changes and modifications without departing from the general scope of this invention. It is intended to include all such modifications and alterations within the scope of the present invention. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A decontamination apparatus comprising:
a motorized base comprising a transport system that is operable to move the decontamination apparatus;
a plurality of UVC bulbs that are adjustably coupled to the motorized base to be independently-positionable relative to each other, wherein each of the UVC bulbs emits UVC light; and
a controller that stores a learned route to be traveled autonomously by the decontamination apparatus from a starting point to a destination during a decontamination process, and controls operation of the transport system to move the decontamination apparatus along the learned route.

2. The decontamination apparatus of claim 1, wherein the transport system comprises a plurality of wheels, and a motor that drives at least one of the plurality of wheels.

3. The decontamination apparatus of claim 1, wherein the controller is configured to control the transport system to reposition the decontamination apparatus from the starting point, where a surface is shielded from the UVC light emitted by the plurality of UVC bulbs, to another location along the learned route where the surface is exposed to the UVC light emitted by at least one of the plurality of UVC bulbs.

4. The decontamination apparatus of claim 1 further comprising a proximity sensor that senses an obstruction interfering with movement of the decontamination apparatus between the starting point and the destination, and transmits a signal that is received by the controller to interrupt movement of the decontamination apparatus along the learned route.

5. The decontamination apparatus of claim 1, wherein the plurality of bulbs are supported at an elevation vertically above the motorized base.

6. A decontamination apparatus comprising:
a motorized base comprising a transport system that is operable to move the decontamination apparatus over a floor;
a plurality of UVC bulbs that each emit UVC light supported by the motorized base;
a sensor that detects a marking on the floor defining a desired route to be traveled by the motorized base during a decontamination process;
a controller that controls operation of the transport system to move the motorized base supporting the plurality of UVC bulbs over the floor along the desired route; and
a cord that conducts electricity between a wall outlet and the motorized base and is flexible to be laid onto the floor to define the desired route, wherein the sensor comprises a cord sensor that detects a quality of the cord on the floor for the controller to control operation of the transport system to cause the motorized base to travel over the floor along the desired route defined by the cord.

7. The decontamination apparatus of claim 6, wherein the transport system comprises a plurality of wheels, and a motor that drives at least one of the plurality of wheels.

8. The decontamination apparatus of claim 6, wherein the plurality of bulbs are adjustably coupled to the base to be independently-positionable relative to each other.

9. The decontamination apparatus of claim 6, wherein the sensor is a color sensor that detects a color of the marking and the controller controls operation of the transport system based on a contrast between the color of the marking relative to a floor color.

10. The decontamination apparatus of claim 6 further comprising a retractor that collects the cord as the motorized base travels along the desired route during the decontamination process.

11. The decontamination apparatus of claim 6, wherein the cord sensor senses a color of the cord on the floor.

12. The decontamination apparatus of claim 6, further comprising:
a spool operable to wind the cord as the motorized base travels along the desired route defined by the cord.

13. The decontamination apparatus of claim 12, wherein the spool is operable to wind the cord approximately at a rate that the motorized base travels along the desired route defined by the cord.

14. The decontamination apparatus of claim 13, wherein the rate that the motorized base travels along the desired route defined by the cord is determined based at least on one or more of a signal from a drive control, a sensed rate of travel based on a signal from the sensor, a calculated rate at which the motorized base is traveling from GPS signals, or any other sensed or calculated value indicative of the rate at which the motorized base travels along the desired route defined by the cord.

15. The decontamination apparatus of claim 12, wherein the spool is arranged at a rear of the motorized base to collect segments of the cord after the motorized base has traveled over the segments.

16. The decontamination apparatus of claim 6, further comprising:
a proximity sensor configured to detect a foreign object as the decontamination apparatus approaches the foreign object.

17. The decontamination apparatus of claim 16, wherein the proximity sensor is configured to send a signal to the controller in response to detecting the foreign object as the decontamination apparatus approaches the foreign object.

18. The decontamination apparatus of claim 17, wherein, in response to receiving the signal from the proximity sensor, the controller is configured to perform one or more of deactivating the motorized base to stop the decontamination apparatus before the decontamination apparatus makes contact with the foreign object, deactivating the plurality of UVC bulbs to cause premature termination of a decontamination process, or inform, by an indicator, an operator of premature termination of a decontamination process.

* * * * *